United States Patent [19]
Antich et al.

[11] Patent Number: 5,583,908
[45] Date of Patent: Dec. 10, 1996

[54] MEGAVOLTAGE SCANNING IMAGER AND METHOD FOR ITS USE

[75] Inventors: Peter P. Antich, Richardson; Jon A. Anderson, Plano; Ervin J. Fenyves, Dallas, all of Tex.

[73] Assignee: Board of Regents, The University of Texas System, Austin, Tex.

[21] Appl. No.: 411,387

[22] Filed: Mar. 28, 1995

Related U.S. Application Data

[63] Continuation of Ser. No. 56,240, Apr. 30, 1993.

[51] Int. Cl.⁶ .................................................. G01N 23/201
[52] U.S. Cl. ......................... 378/65; 378/5; 378/6; 378/87
[58] Field of Search ........................ 378/5, 6, 65, 87

[56] References Cited

U.S. PATENT DOCUMENTS

| | | | |
|---|---|---|---|
| 3,965,353 | 6/1976 | Macovski | 250/336 |
| 4,124,527 | 11/1978 | Kauffman | 252/408 |
| 4,150,292 | 4/1979 | Ter-Pogossian | 250/363 S |
| 4,739,521 | 4/1988 | Akimoto | 455/612 |
| 4,756,866 | 7/1988 | Alvarez | 376/157 |
| 4,816,683 | 3/1989 | Marsden | 250/385.1 |
| 4,942,302 | 7/1990 | Koechner | 250/368 |
| 4,980,901 | 12/1990 | Miller | 378/45 |
| 4,992,746 | 2/1991 | Martin | 328/235 |
| 5,073,913 | 12/1991 | Martin | 378/34 |
| 5,103,098 | 4/1992 | Fenyves | 250/368 |
| 5,220,170 | 6/1993 | Cox et al. | 250/366 |

OTHER PUBLICATIONS

Lewis et al, "A Megavoltage CT Scanner for Radiotherapy Verification," Phys. Med Biol., 37:10, p. 1985–1999 (1992).
Benjamin and Macovski, "Stimulated Positron Emission for 3–D Tomographic Imaging and Bone Studies–Part I: Method Feasibility and System Considerations", IEEE Transactions on Medical Imaging, 8(2):113–124 (1989).
Anderson et al, "Stimulated Positron Emission Analysis Techniques for the Quantitative Assessment of Fluorine in Bone", the QIEEE Transactions on Nuclear Science, 38(2):713–718 (1991).
Antich et al, "Development of a High Resolution Scintillating Fiber Gamma Ray Telescope", Nuclear Instruments and Methods in Physics Research A297:514–520 (1990).

*Primary Examiner*—Craig E. Church
*Attorney, Agent, or Firm*—Arnold, White & Durkee

[57] ABSTRACT

Apparatus for generating a high contrast image of a living subject includes an X-ray source capable of generating an X-ray beam having an energy between about 4 MeV and about 40 MeV, means for directing the X-ray beam generated by the X-ray source to a preselected area of the body of a living subject, and at least one scintillating detector capable of detecting photons which are generated as a result of the interaction of the X-ray beam with the body of the living subject.

12 Claims, 6 Drawing Sheets

MEGAVOLTAGE SCANNING IMAGER AND METHOD FOR ITS USE

This application is a continuation of co-pending application Ser. No. 08/056,240, filed on Apr. 30, 1993.

BACKGROUND OF THE INVENTION

The preset invention relates to a method and apparatus for generating a high contrast image of a living subject using high energy X-rays.

X-rays have been used for some time to generate images of living subjects. In previous X-ray imaging technology, X-rays are transmitted toward the living subject from an X-ray source, and are transmitted through the tissue to be imaged. The degree of transmission of the X-rays in different parts of the irradiated area of tissue varies depending on the nature of the matter or tissue through which it must pass. By measuring or determining the degree of transmission of the X-rays through the target area, an image of the irradiated area can be created.

If high-energy X-rays are used in standard X-ray imaging technology, the resulting image will have relatively little inherent contrast, especially if the area of tissue imaged consists only of soft tissue, as compared to a combination of soft tissue and bone.

The problem of generating high contrast images of soft tissue is especially important in oncologic imaging. The ability to distinguish tumors from surrounding soft tissue is extremely useful in diagnosis and treatment of cancer.

Furthermore, it is necessary to image these structures both in their three-dimensional relationship (3-D or cross-sectional images) and from the "beam's eye" point of view, as projected 2-D images, in order to support the treatment of tumors by radiation therapy. In this therapeutic modality, high-energy X-ray beams are placed so as to deliver the greatest possible dose to the tumor and to spare as much as possible normal tissues. Currently, films or electronic images are used to plan and verify the proper placement, shape and dimension of the treatment beam, while cross-sectional and volumetric images are obtained by computed tomography (CT) or magnetic resonance imaging (MRI). The information obtained from these various modalities is then manipulated by computer and used to design a patient-specific treatment plan. These activities are lengthy, expensive, and potentially fraught with uncertainties deriving from the lack of a direct, fast method for visualizing the treatment volume within the patient in the actual device and in the position used for treatment, as well as the need for extensive computer modeling and simulation.

Finally, even more than in diagnostic imaging modalities, a method capable of giving real-time images would be of particular usefulness when used in support of radiosurgery. Such a method does not exist today. Radiosurgery is so critically dependent upon correct beam positioning that a special fixture must be constructed to guide the therapy beams delivering the treatment, which is typically limited to a single session. This has the disadvantage that fractionated treatments (treatments delivered over several sessions) are impossible or, at best, are difficult and potentially less precise. (Fractionated treatments are the mode of choice in standard therapy, offering significant biological advantages.) A method for on-the-spot, real time visualization, requiring only a modest X-ray dose, would offer the advantage of making fractionated radiosurgery practical, and both fractionated and single-dose therapy more precise and accurate.

Therefore there is a need for improved imaging apparatus and methods which have fewer problems than the prior technology.

SUMMARY OF THE INVENTION

The present invention relates to apparatus for generating a high contrast image of a living subject which includes an X-ray source capable of generating an X-ray beam having an energy between about 4 MeV and about 40 MeV, a mechanism for directing the X-ray beam generated by the X-ray source to a preselected area of the body of a living subject, and at least one scintillating detector capable of detecting photons or gamma rays which are generated as a result of the interaction of the X-ray beam with the body of the living subject.

The apparatus preferably includes a plurality of scintillating detectors capable of detecting photons or gamma rays which are generated as a result of the interaction of the X-ray beam with the body of the living subject, with two or more of the scintillating detectors being located at opposite sides of the body of the living patient. Further, the apparatus can include a plurality of position sensitive photomultipliers, with each position sensitive photomultiplier being coupled to at least one scintillating detector.

The apparatus preferably includes a computer for analyzing data collected from the scintillating detectors. The computer can compare the time of emission of an X-ray pulse by the X-ray source with the times at which photons are detected by the scintillating detectors in order to determine which detected photons likely resulted from an interaction of the pulsed X-ray beam with the subject's body.

The X-ray source preferably is capable of generating a pulsed X-ray beam, and the apparatus can optionally include a scanner for scanning the X-ray beam across a preselected area of the patient's body.

The present invention also relates to a method for generating a high contrast image of a living subject. In one embodiment, the method includes the steps of (a) emitting a pulsed X-ray beam having an energy between about 4 MeV and about 40 MeV, (b) directing the X-ray beam to a preselected area of the body of a living subject, (c) detecting with a plurality of mutually opposing detectors the gamma rays or photons generated as a result of pair production or photonuclear reactions when the X-ray beam interacts with the subject's body, (d) determining the site in the subject's body at which the X-ray beam interacted with the body by determining the point of intersection between (1) the line connecting the two points on the mutually opposing detectors at which gamma rays or photons were detected and (2) the path of the X-ray beam at the time at which the gamma rays or photons were detected by the detectors, thereby generating an image data point, (e) repeating steps (a)—(d) until sufficient data points are obtained from which to generate an image of the preselected area of the body of the living subject across which the X-ray beam was scanned.

In another embodiment, the method includes the steps of (a) emitting a pulsed X-ray beam having an energy between about 4 MeV and about 40 MeV, (b) directing the X-ray beam to a preselected area of the body of a living subject, (c) detecting with a plurality of mutually opposing scintillating detectors the gamma rays or photons generated as a result of pair production or photonuclear reactions when the X-ray beam interacts with the subject's body, (d) determining the site in the subject's body at which the X-ray beam interacted with the body by determining the point of intersection between (1) the plane defined by two parallel elongated scintillating detectors in which gamma rays or photons were detected and (2) the path of the X-ray beam at the time at which the gamma rays or photons were detected by the scintillating detectors, thereby generating an image data point, and (e) repeating steps (a)–(d) until sufficient data points are obtained from which to generate an image of the preselected area of the body of the living subject across which the X-ray beam was scanned.

The high energy X-rays used in the present invention interact with the living tissue being imaged, and more specifically they excite such tissue, resulting in the production of a positron-electron pair. The positron subsequently annihilates (typically at some distance from the point where it was created), causing the emission of two 511 kev photons in exactly opposite directions from the site of the interaction.

One further mode of interaction which results in the emission of a positron is the photonuclear interaction, in which an X-ray of the primary beam ejects a neutron from a nucleus in the subject. The nucleus is left in an unstable configuration and subsequently decays, emitting a positron. A crucial difference between these two interactions is that pair production results in an immediate positron, but the photonuclear interaction results in the emission of a positron over a time interval ranging from seconds to minutes and hours. Thus the effects do not overlap in time and both phenomena could be used, by obtaining prompt and delayed images, to derive information on anatomical details in the first case, and specific information on atomic composition of the body in the second.

The light quanta are detected on opposite sides of the site of interaction by detectors, with coincidence of detection at two opposing detector locations permitting the determination of the site of interaction (i.e., the site of the interaction is the intersection of the line defined by the two detection points with the plane of irradiation).

The X-ray beam used in the present invention can suitably have an energy between about 4 and about 40 MeV, and can be generated by a pulsed X-ray source such as a medical linear accelerator. The energy is preferably between about 15–40 MeV, and most preferably between about 15–18 MeV. When the energy used is between about 4–15 MeV, the result will be production of positron-electron pairs, while at energies greater than about 18 MeV, photonuclear reactions will also occur.

The present invention uses high energy irradiation to produce high contrast, fast cross-sectional or three-dimensional images of soft tissues. The images generated by the present invention are sensitive to atomic number, density, and elemental composition of the body tissues irradiated. The present invention is especially useful with respect to imaging the tissue of cancer patients, because it can be used to plan treatment (such as radiation therapy), verify the execution of the treatment, and to evaluate the patient's response to the therapy. Similarly, the present invention can be used to improve accuracy in the delivery of radiosurgery, i.e. to verify beam placement prior to the administration of a dose of radiation to the patient's body, or to dynamically follow the movement of a target organ. Further, the present invention is well-suited to automation, for example in conjunction with computer controlled motion (of the linear accelerator, beam shaping devices, or of the table on which the patient lies during imaging).

The present invention can provide a synchronous three-dimensional image of all organs and tissues in the X-ray beam path with a single fixed projection of the beam. The method and apparatus of the present invention intrinsically involve a high signal to noise ratio, thus improving the quality of the image generated while permitting the use of lower X-ray doses.

BRIEF DESCRIPTION OF THE DRAWINGS

FIG. 1 shows a megavoltage scanner in accordance with the present invention in a configuration suitable for radiation therapy applications.

DETAILED DESCRIPTION OF SPECIFIC EMBODIMENTS

An apparatus in accordance with the present invention includes a high-energy X-ray source capable of generating a pulsed beam. The energy of the beam generated by the source should be preferably between 4 MeV and 40 MeV. The usual energy range is 4 to 25–30 MeV. Suitable linear accelerators are produced by Varian (Palo Alto, Calif. 94304) as well as by Siemens, Philips, and other companies.

Figure 1A:
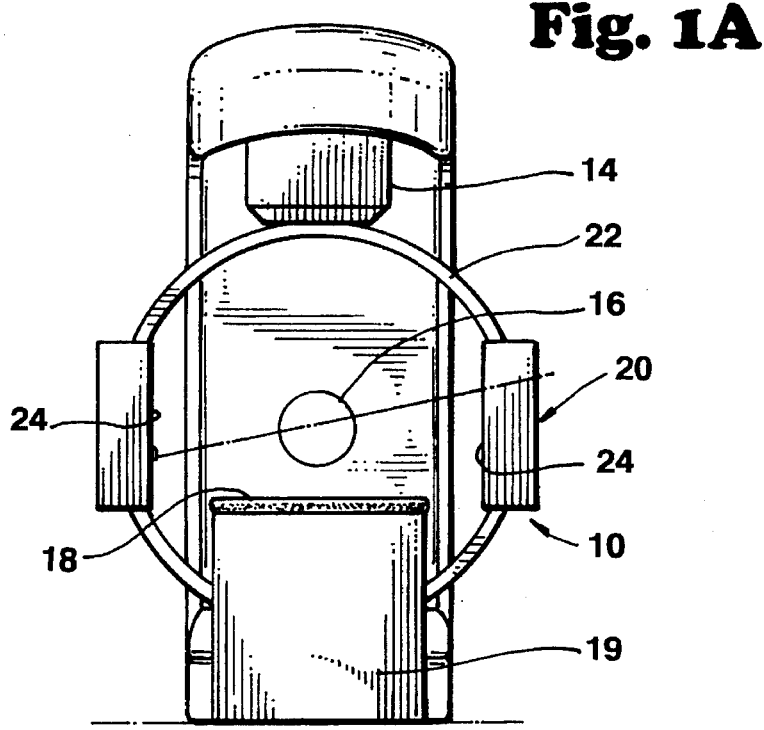
FIG. 1A is a front view and FIG. 1B is a side view.
Figure 1B:
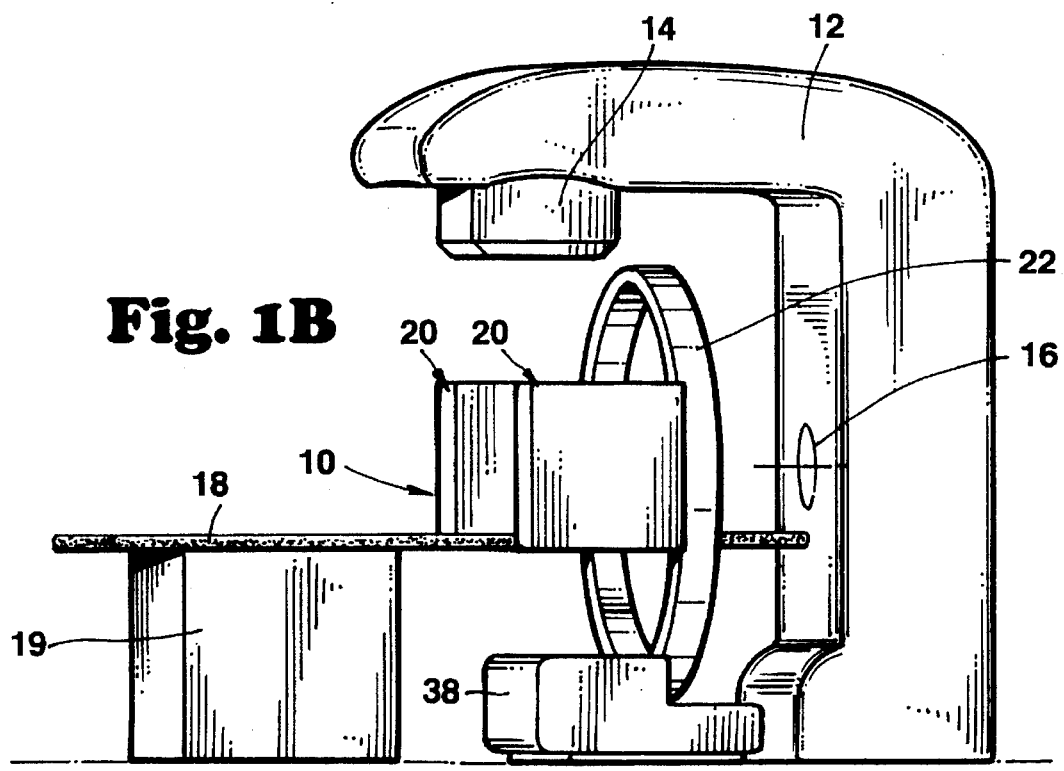

FIG. 1 shows the megavoltage scanner 10 in a configuration suitable for radiation therapy applications. The linear accelerator accelerates a beam of electrons to a selected energy and directs them at a target to produce an X-ray beam. The target and the X-ray collimators (electronic or mechanical beam-shaping devices) are placed in the head 14 of the therapy unit, which is mounted on a gantry 12. The linear accelerator is located in the gantry 12. The equipment is capable of rotating around one or more axes 16. The patient is supported on a couch 18 that is located on top of a patient support 19, so that the primary beam can irradiate the desired anatomical features of the patient.

Figure 2:
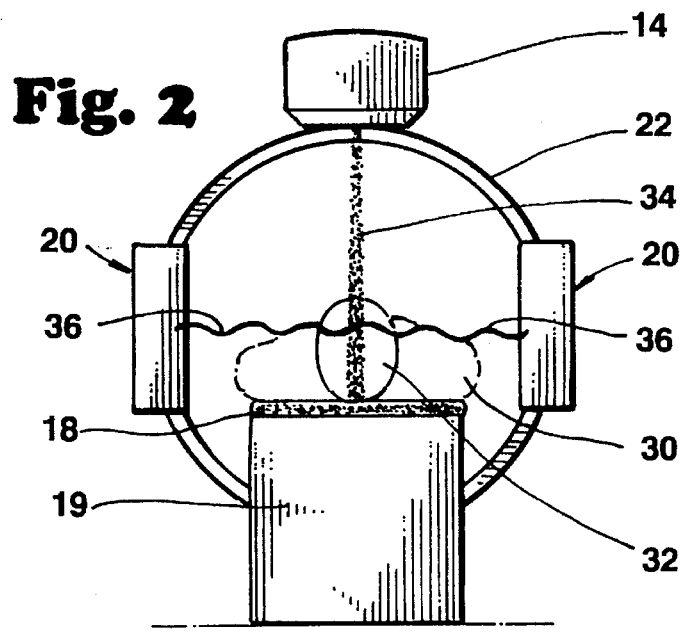
FIG. 2 shows a patient, as seen from the top of his head, in a megavoltage scanner in accordance with the present invention.
Figure 3:
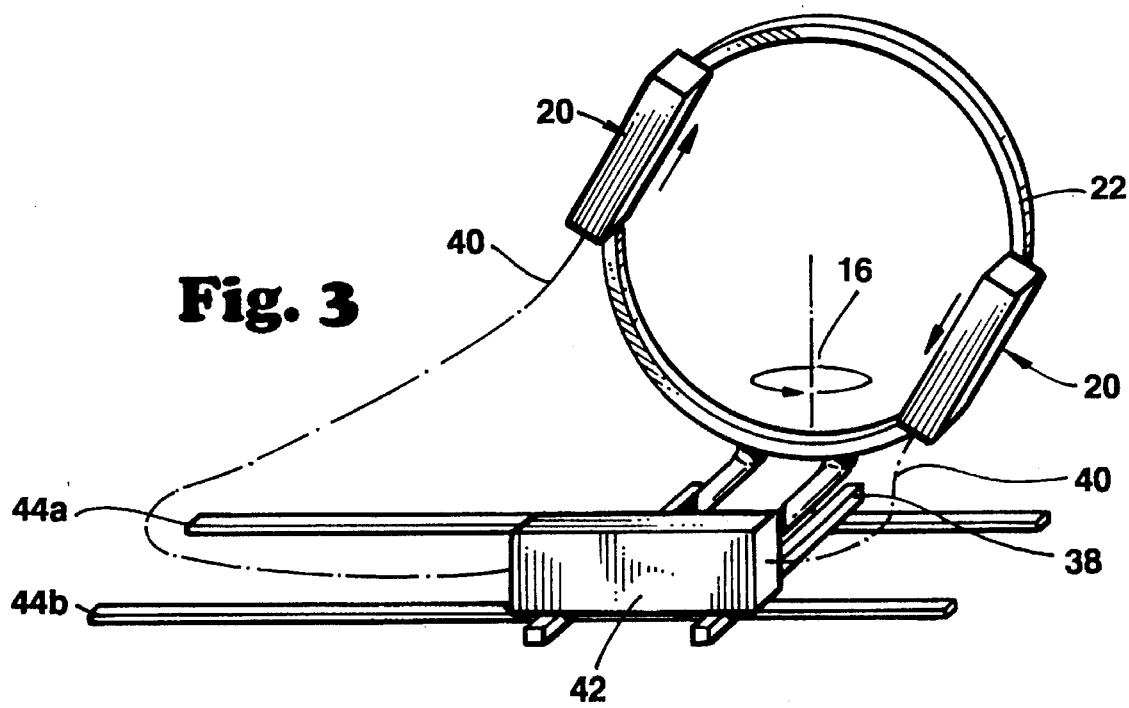
FIG. 3 shows detector apparatus in accordance with the present invention, with the gantry on which the detectors are mounted being self standing and removable from the accelerator.

The detector assemblies 20 of the megavoltage imager are mounted on an appropriate support 22 and are capable of rotating around the axes 16, and of other movements as necessary. Alternatively, more complex robotic arms can be employed. What is required is that the detectors 20 are placed so that the line joining their centers 24 (normal to their faces) is approximately orthogonal to the beam center line and to the long axis of the subject's body. Thus the three directions (beam axis, patient axis, detector axis) form a Cartesian coordinate system. This can also be seen in FIG. 2, which shows the patient 30 as seen from the top of his head 32, with the therapy head 14 emitting an X-ray beam 34. The two gamma-rays 36 emitted in a pair-production event are shown impinging upon the two parallel detector assemblies 20. The detectors 20 are mounted on a C-arm support 22, which in turn is mounted on a base 38 so that they can be positioned as needed. The entire apparatus can be mounted on the linear accelerator or can be self-standing and removable from the beam (FIG. 3). In the embodiment of FIG. 3, rails 44a and 44b are used to permit movement and precise positioning of the detector apparatus with respect to both the patient and the therapy machine.

The scintillating optical fibers of the detector assemblies 20 are spliced onto non-scintillating optical fibers 40 which then carry light signals to the electronics, located in an enclosure 42, which is appropriately shielded against ionizing radiation and EM fields. In another embodiment of the invention, the electronics could be located elsewhere.

The X-ray beam generated by the source can be a pencil beam (a beam having a small cross-sectional dimension and having a round, elliptical, rectangular, or other shape), a planar or sheet beam, or a beam with a more complex form.

The present invention can also include means for creating magnetic fields that will permit more precise reconstruction of the structures in the X-ray beam's path. For example, a magnetic field perpendicular to the X-ray beam may be used to increase the resolution along the single direction of the pencil beam. Another possibility is the use of parallel opposed X-ray beams. Current radiotherapy equipment, where the head of the therapy unit can be rotated around the patient, is routinely capable of providing such a pair of beams. In this case two images would be obtained and intercompared. The first image, obtained with the beam traveling in a certain direction x, is predominantly affected by positron smearing in that direction because the electron-positron pair have their greatest component of momentum along the +x direction. The second image will similarly be most affected in the −x direction. If the centroid of the image is considered, a point will therefore appear displaced in the +x direction in the first image, in the −x direction in the second. The two images can then be averaged or treated with more sophisticated algorithms to give a truer image of the point.

The apparatus can also include a scanning mechanism for scanning the X-ray beam generated by the X-ray source across a preselected area of the body of a living subject. This scanning of the beam is preferably done electronically in a preset sequence, similar to the rastering in a television screen. Thus the region of the body is scanned with the X-ray beam in a sequential fashion.

Two preferred versions of the scanning device are described as follows. In the first, the electron beam within the accelerator is moved about its central position using at least two orthogonal dipolar magnets. The intensity of the current (thus, the magnetic field intensity) in each of the two magnets is varied according to a periodical law (e.g. with a sinusoidal time dependence). As a consequence of this variation the electron beam impinges on the conversion target at different positions, creating by bremsstrahlung an X-ray beam of origin and direction variable according to the same periodic law. A second alternative takes advantage of mechanical beam-shaping devices such as those present in the head of conventional therapy equipment. These use diaphragms which allow the passage of an X-ray beam only along certain directions, and stop it at all other directions. The diaphragm could be similar in construction and function to those already present in current therapy machines, e.g. those equipped with independently moving jaws operating under computer control. In either case the result would be that only the targeted region of the body is irradiated, and that different portions of this volume are irradiated at different times in a preselected fashion (scanned). The scanning devices can be located in therapy head 14, where beam collimators are located for conventional therapy applications.

Another component of the present invention is a plurality of scintillating detectors, for example scintillating plastic fibers. Two or more of the scintillating detectors are located at opposite sides of the body of the living patient, so that they can detect the oppositely-directed photons that are generated as a result of the interaction of the X-ray beam with the patient's tissue. The scintillating detectors can be made of intersecting cylinders, or of single crystals. Alternatively, elongated detectors parallel to each other and perpendicular to the scanning line beam may be employed.

Figure 4A:
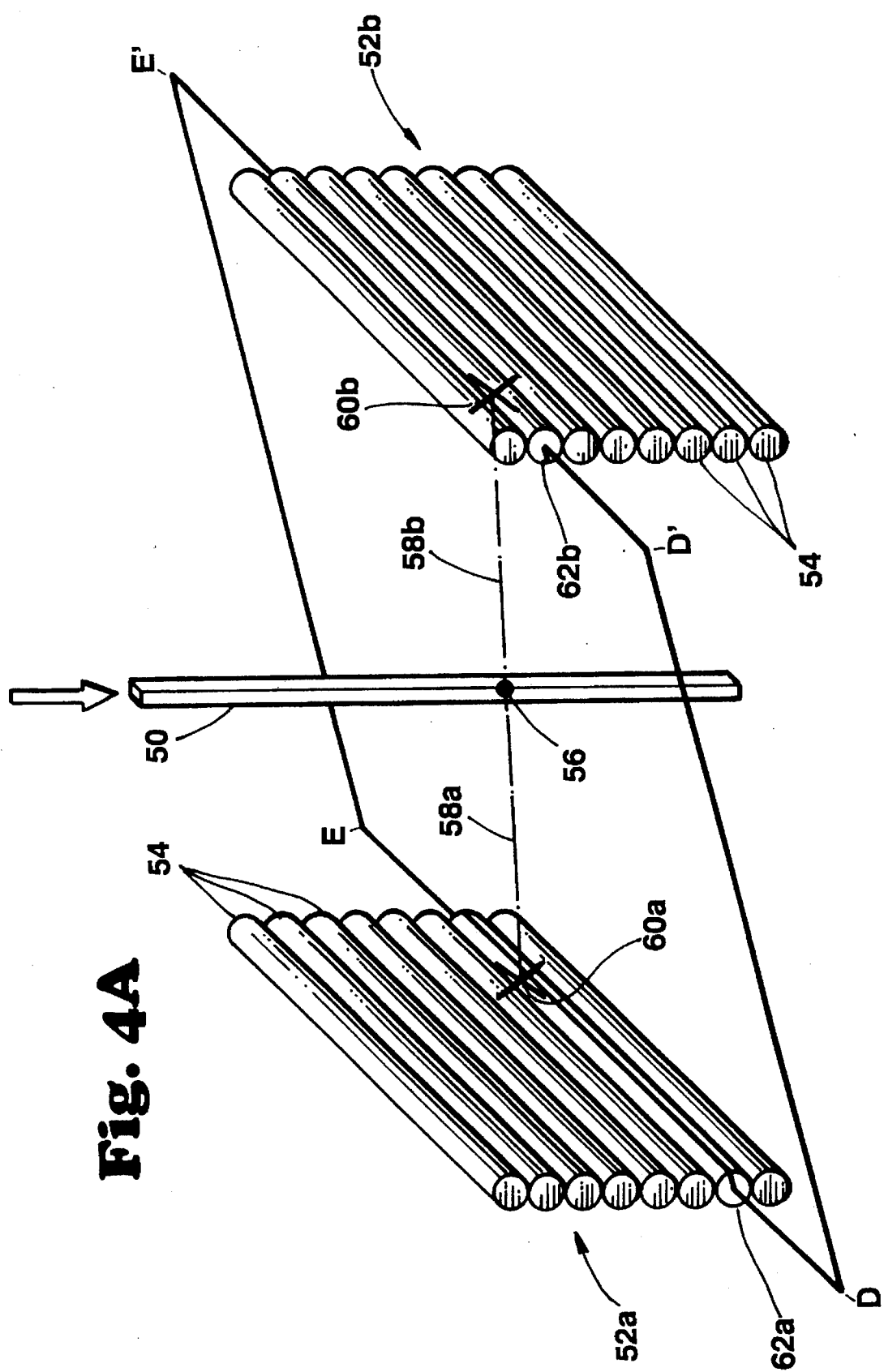
FIG. 4A shows a preferred configuration of an X-ray beam and detector assemblies in accordance with the present invention.

One especially preferred configuration of X-ray beam 50 and detector assemblies 52a and 52b is shown in FIG. 4A, which also shows how this configuration may be used to determine uniquely the point at which a positron annihilation has occurred. An incident x-ray beam 50 of pencil form irradiates a volume which is at least partially enclosed by planar detector assemblies or arrays 52a and 52b. The detector arrays 52 are formed from a large number of parallel, elongated elements 54, which may be scintillating crystals or, more preferably, plastic scintillating optical fibers. The detector arrays 52 may have a single layer, as shown, or may have multiple layers. The detector assemblies should be either parallel, as shown, or may be tilted. If they are tilted, the individual elements in assembly 52a must still be parallel to the individual elements in assembly 52b.

If an electron-positron pair is generated by the incident beam 50 at location 56, the positron will rapidly be slowed and will annihilate, usually producing two 511 keV photons that are collinear and which travel in opposite directions. In common with all positron emission tomography schemes, the positron will travel only a small distance from its point of creation before it will be annihilated; thus the annihilation gammas can be assumed to originate essentially at the point 56 where the electron-positron pair was created. Two annihilation gamma rays 58a and 58b generated at point 56 following interaction of the incident beam 50 are shown by dotted lines in FIG. 4A. Coincidence gating of the photodetectors attached to detector array 52a and to detector array 52b will be used to insure that only those annihilation events which cause scintillation events in both arrays will be processed. Two bold cross-marks 60a and 60b on the figure illustrate the sites of two such gamma-ray interactions. Following the interaction of the annihilation gammas in the detector elements, light will be generated which will be conducted to the end of the affected fibers 62a and 62b. These ends would be joined to photodetectors such as position sensitive photomultipliers (not shown in FIG. 4A), so that the affected fibers could be identified.

Depending on how the fibers 54 may be coupled together, fibers immediately adjacent to the principal fibers 62a and 62b may also conduct light to the photodetectors, in which case the principal fibers 62a and 62b would be determined by an interpolation algorithm such as determining the centroid of the observed light distribution at the photodetector. Since the two fibers are parallel, they define a plane DD'EE'. This plane contains the original trajectories of the annihilation gammas, shown in dotted lines 58a and 58b. The plane DD'EE' intersects the incident X-ray beam 50 at the unique point 56, which was the point at which the annihilation gamma rays were emitted. Thus, given a knowledge of the line of incidence of the irradiating beam 50 and knowledge of the locations of fibers 62a and 62b, the point of interaction 56 can be uniquely determined. This is true for all situations such that the incident beam is not contained in the plane DD'EE'. In a particularly preferred implementation, the incident beam 50 is perpendicular or nearly perpendicular to a plane that is itself perpendicular to the two detector arrays 52a and 52b, and which is parallel to the fibers which make up the arrays or assemblies 52a and 52b.

Irradiation of the subject's tissue with high energy X-rays can cause, in addition to the pair production interaction, Compton scattering of photons. The Compton scattered photons are extraneous events in the method of the present invention, and will reduce the contrast and overall quality of the image if they are not screened out at some point in the imaging process.

Fenyves U.S. Pat. No. 5,103,098, which is incorporated here by reference, discloses detector configurations suitable for use in the present invention. The distributed detectors can also include a plurality of position sensitive photomultipliers which are coupled to the scintillating detectors, as disclosed and shown in Fenyves.

The scintillating detectors can be part of a distributed detector system, comprising opposing distributed detectors for detecting gamma rays originated by pair production or photonuclear reactions. Each distributed detector preferably includes means for recording double Compton interactions, meaning two consecutive interactions of the same photon originated by pair production or photonuclear reaction. Software can make use of the double Compton kinematics to reduce noise and enhance the image.

In a double Compton event, one of the two gamma rays generated by the positron's annihilation interacts twice within the same detector (the other gamma may have one or two Compton interactions). The software uses the information on the position and deposited energy for each of the two interactions of that gamma ray to reconstruct its line of flight (electronic collimation). The event would then be accepted (or rejected as noise) if this line of flight did (or did not) coincide with the line joining the position of the first interaction of this gamma ray with the position of the interaction of the other annihilation-produced gamma ray.

Figure 4B:
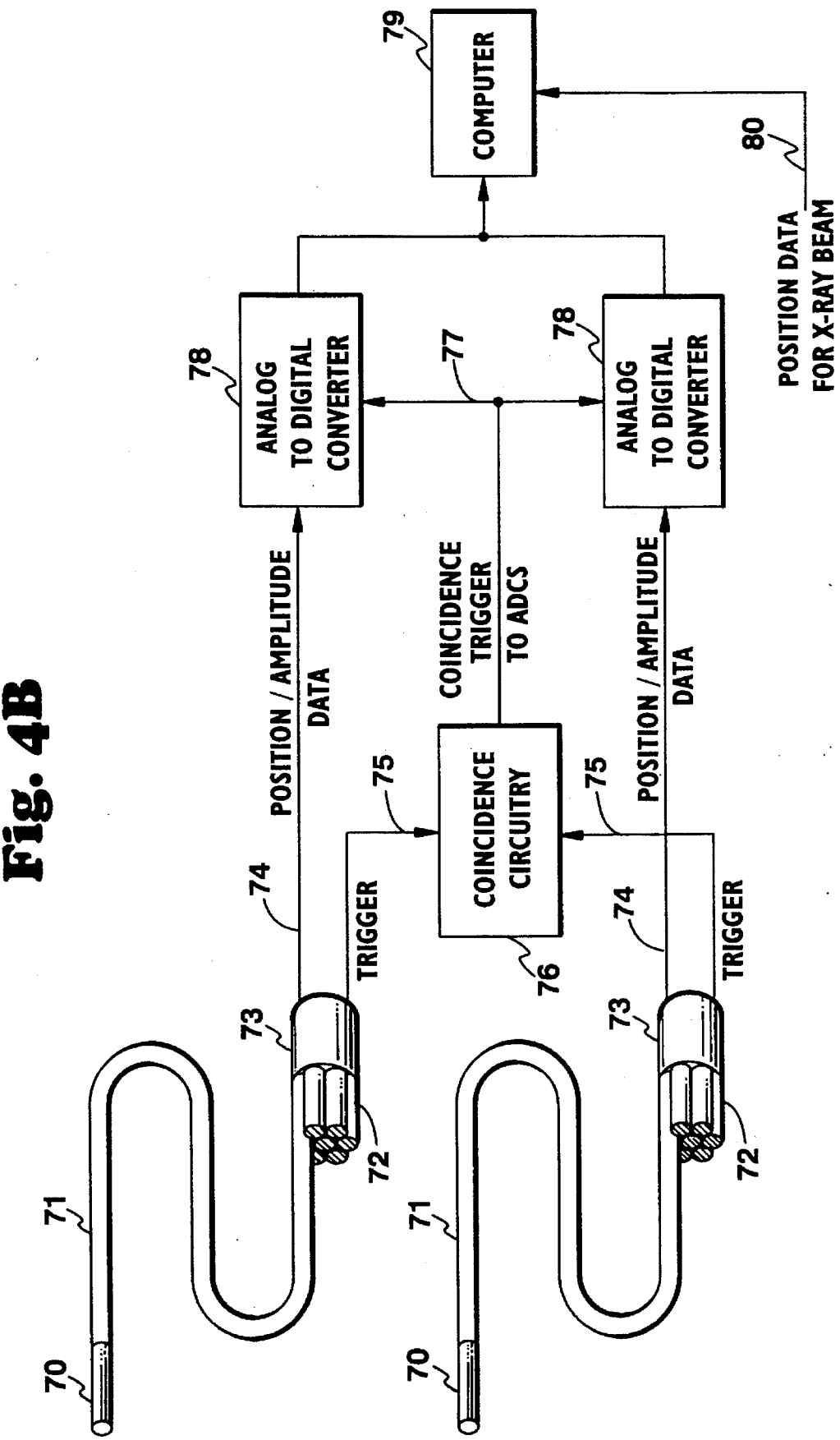
FIG. 4B shows a preferred means for connecting the detector apparatus to a computer in accordance with the present invention.

The system also includes a computer for using the data collected by the detectors to generate an image. FIG. 4B shows how the computer may be connected to a detector system such as the one illustrated in FIG. 4A. Two scintillating fibers 70, one from each array 52 shown in FIG. 4A, are connected to position sensitive photomultipliers 73 by means of nonscintillating fibers 71. Typically, these nonscintillating fibers would be assembled into bundles 72 that would be coupled to the photomultipliers. Trigger signals 75, indicating the occurrence of a scintillation detection by the photomultiplier are connected to coincidence circuitry 76. The arrival of essentially simultaneous triggers from both photomultipliers will generated a coincidence trigger signal 77 that causes analog-to-digital converters 78 to make a conversion of the multiple anode signals 74 carrying the position and amplitude information available from the position sensitive photomultipliers 73. Typically, the analog-to-digital converters 78 will have local memory for storing a limited number of events. At intervals, this data will be downloaded to the computer 79 for processing and image reconstruction. The computer will also have data inputs 80 describing the position of the incident photon beam from the x-ray device.

The computer can analyze and compare the time of emission of the X-ray pulse by the X-ray source with the times at which photons are detected by the scintillating detectors. The X-ray generator will typically be rapidly pulsed, and pair production will occur only during the pulse, while photonuclear reactions will give rise to delayed positrons. The computer can determine when detected photons coincide or fail to coincide in time with the X-ray pulse, and this can be used by the computer to isolate the two classes of events. Further, time-of-flight analysis (comparison of the time elapsed between X-ray pulse emission and the detection of coincident opposing photons by the scintillating detectors) provides a useful means of eliminating extraneous events or "noise." In this regard, the use of the new detector system is especially important, because such detectors have nanosecond timing resolution, which is far superior to many other detector schemes.

In one implementation of this invention, the computer system would consist of a specialized hardware front-end that performs the preliminary processing on the data and a fast and powerful general purpose processor such as an engineering work station. Such computers include the RS-6000 family available from the IBM Corporation and various workstations available from the Sun Corporation.

Figure 5:
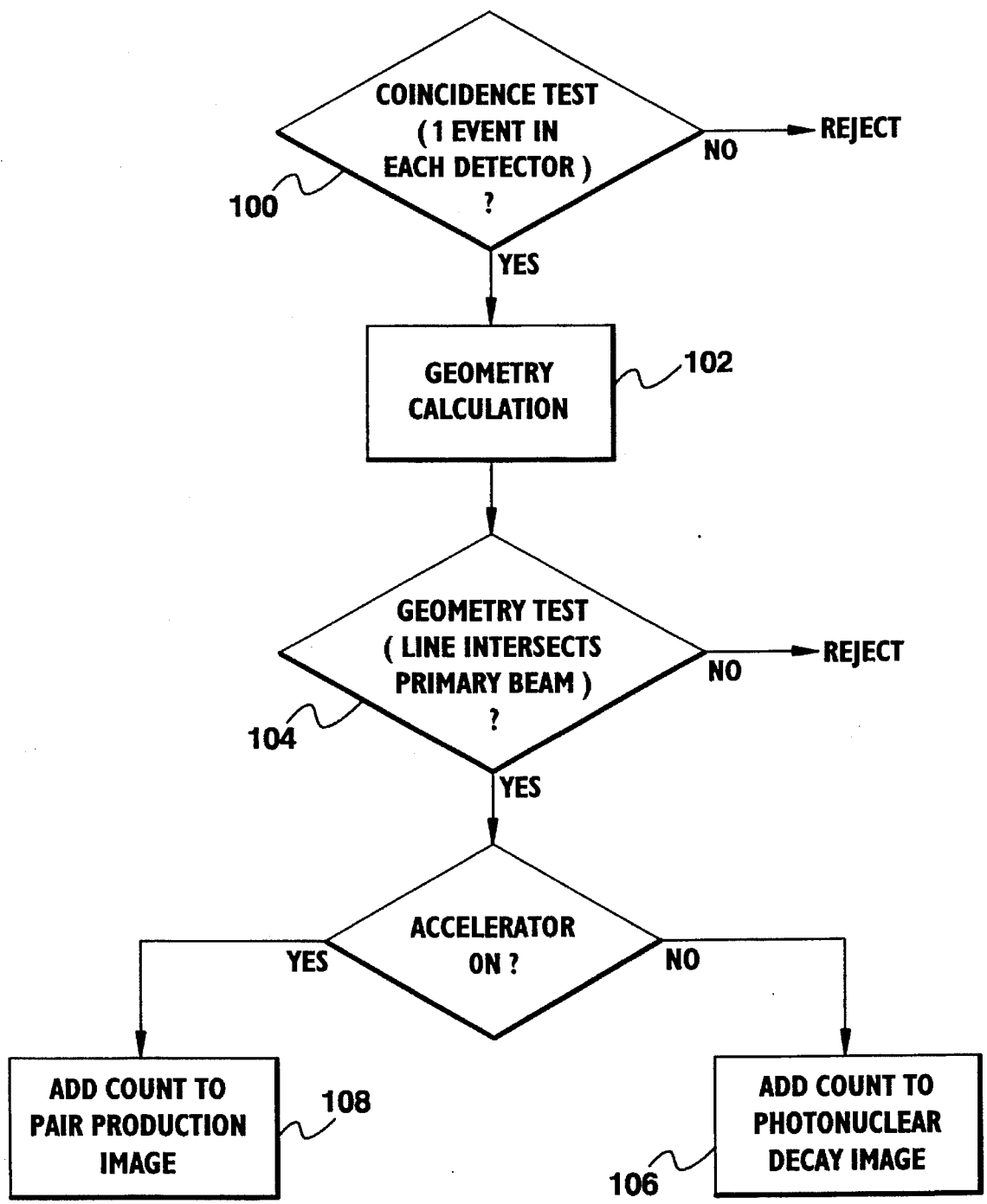
FIG. 5 shows a process in accordance with the present invention for reconstructing an image from data obtained from detectors.

The reconstruction algorithm depends on the particular detector configuration implemented. FIG. 5 illustrates the reconstruction process for the particularly preferred detector embodiment shown in FIG. 4, which employs a primary X-ray beam in pencil form. If both of the opposing detectors shown in FIG. 4 register a count in temporal coincidence, then the event is judged to be valid; otherwise it is rejected (100). The location of the annihilation event can be determined by calculating the intersection of the plane DD'–EE' with the known location of the incident X-ray beam (102). Furthermore, if a fully position sensitive detector assembly (i.e. one which can locate not only the fibers 62a and 62b in which the radiation interactions occurred, but also the points along the lengths of the fibers at which the interactions occurred) is used, then an optional second noise suppression test can be applied. For a valid event in this case, the line connecting these points, shown by the crosses 60a and 60b in FIG. 4, must intersect the known position of the incident X-ray beam (104). If the event is judged to be valid, then a count will be added to the reconstructed image at the calculated location. Two images are generated, based on whether the detector responded while the X-ray generator was off (counts due only to the decay of photonuclear reaction products) (106) or while the generator was on (counts due to both pair production and photonuclear decay products) (108).

Figure 6:
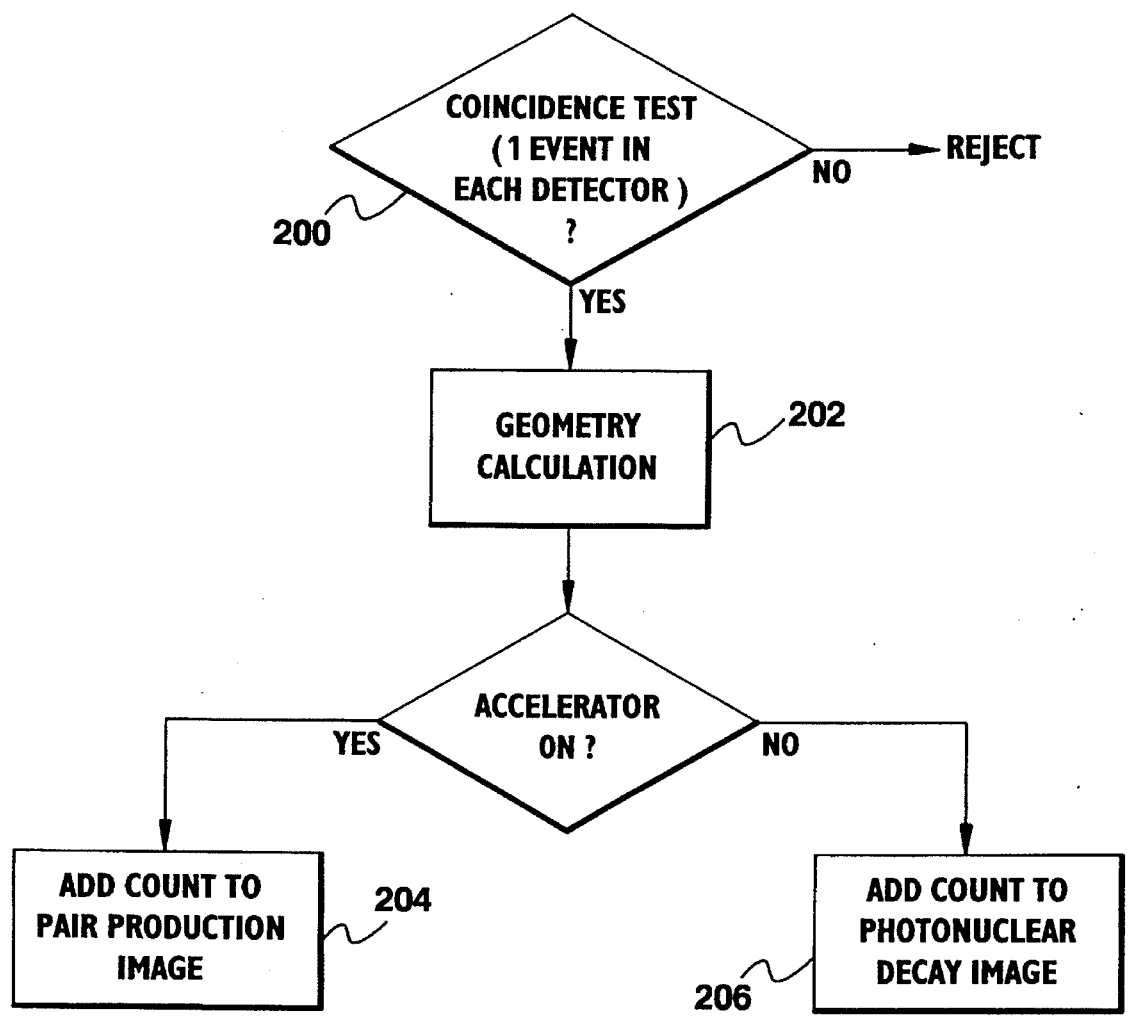
FIG. 6 shows an alternative process in accordance with the present invention for reconstructing an image from data obtained from detectors.

The reconstruction process for a second preferred embodiment, employing an incident X-ray beam in sheet form, is shown in FIG. 6. This case requires the use of fully position sensitive detectors. The event is tested for coincident response in both detector assemblies (200), and if it is found to be valid, the intersection of the line connecting the coincident interactions in the two detectors and the known plane of the incident beam is calculated (202). A count is then added to one of the two reconstructed images at the calculated location, the choice of the image being based on whether the x-ray beam was on (204) or off (206) at the time the event occurred.

The preceding description is intended to illustrate specific embodiments of the invention. It is not intended to be a complete list of every possible form that the invention could take. Persons skilled in the relevant art will appreciate that modifications could be made to the specific embodiments disclosed above that would still be within the scope of the invention.

We claim:

1. A method for generating a high contrast image of a living subject, comprising:
   a. emitting a pulsed X-ray beam having an energy between about 4 MeV and about 40 MeV;
   b. directing the X-ray beam to a preselected area of the body of a living subject;
   c. detecting, with position-sensitive scintillating fiber optic detectors which are positioned on opposite sides of the subject's body, gamma rays or photons that are generated as a result of pair production or photonuclear reactions when the X-ray beam interacts with the subject's body, said gamma rays or photons generating light in the fiber optic detectors;
   d. conveying said light to a plurality of position sensitive photomultipliers;
   e. determining, from the light conveyed to the position sensitive photomultipliers, the site in the subject's body at which the X-ray beam interacted with the body;
   f. repeating steps (a)–(e) until sufficient data points are obtained from which to generate an image of the preselected area of the body of the living subject; and
   g. generating another X-ray beam, said beam having a beam energy suitable for radiotherapy of the living subject, and using the image generated in step (f) to direct the beam in order to deliver radiotherapy to an area of the subject's body.

2. The method of claim 1, where the X-ray beam is generated by a linear accelerator.

3. The method of claim 1, further comprising scanning the X-ray beam across a preselected area of the subject's body.

4. The method of claim 1, where a volume of tissue and/or organ in the living ,subject is imaged.

5. The method of claim 1, where multiple radiosurgery treatments are administered to the living subject at different times and the method of steps (a) - (f) is used each time to image the portion of the subject's body to be treated by radiosurgery.

6. The method of claim 1, where the X-ray beam has an energy between about 15 MeV and about 40 MeV.

7. The method of claim 1, where the X-ray beam has an energy between about 15 MeV and about 18 MeV.

8. The method of claim 1, where the X-ray beam is a sheet beam.

9. The method of claim 1, where the X-ray beam is a pencil-shaped beam.

10. The method of claim 1, further comprising recording double Compton interactions in the detectors.

11. The method of claim 1, further comprising comparing the time of emission of the X-ray pulse with the times at which gamma rays or photons are detected by the scintillating detectors.

12. The method of claim 11, where the comparison of the time of emission of the X-ray pulse with the times at which gamma rays or photons are detected by the scintillating detectors is used to distinguish between detected gamma rays or photons resulting from pair production and those resulting from photonuclear interactions.

* * * * *

UNITED STATES PATENT AND TRADEMARK OFFICE
CERTIFICATE OF CORRECTION

PATENT NO. : 5,583,908
DATED : December 10, 1996
INVENTOR(S) : Peter P. Antich, Jon A. Anderson, and Ervin J. Fenyves It is certified that error appears in the above-indentified patent and that said Letters Patent is hereby corrected as shown below:

In Claim 4, at Column 10, line 4, delete "," after "living".

Signed and Sealed this

Fourth Day of March, 1997

Attest:

BRUCE LEHMAN

Attesting Officer     Commissioner of Patents and Trademarks